US009429503B2

(12) United States Patent
Seok

(10) Patent No.: US 9,429,503 B2
(45) Date of Patent: Aug. 30, 2016

(54) METHOD FOR MAKING TEST SPECIMEN AND TEST EQUIPMENT TO EVALUATE THE SAFETY OF PIPING

(71) Applicant: Research & Business Foundation SUNGKYUNKWAN UNIVERSITY, Suwon-si (KR)

(72) Inventor: Changsung Seok, Gwacheon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 229 days.

(21) Appl. No.: 13/890,492

(22) Filed: May 9, 2013

(65) Prior Publication Data

US 2013/0298692 A1 Nov. 14, 2013

(30) Foreign Application Priority Data

May 10, 2012 (KR) .......................... 10-2012-0049732

(51) Int. Cl.
*G01N 3/24* (2006.01)
*G01N 3/08* (2006.01)
*G01N 3/62* (2006.01)

(52) U.S. Cl.
CPC ...... *G01N 3/08* (2013.01); *G01N 3/62* (2013.01); *G01N 2203/027* (2013.01); *Y10T 29/49995* (2015.01)

(58) Field of Classification Search
CPC ..... G01N 2203/027; G01N 3/62; G01N 3/08
See application file for complete search history.

(56) References Cited

U.S. PATENT DOCUMENTS 4,916,954 A * 4/1990 Buzzard .................. G01N 3/08
73/799

8,549,929 B2 * 10/2013 Seok ........................ G01N 3/04
73/851
2011/0094307 A1 * 4/2011 Seok ........................ G01N 3/04
73/851

FOREIGN PATENT DOCUMENTS

JP       2002-267581      9/2002

OTHER PUBLICATIONS

Korean Office Action issued Jul. 5, 2013 in counterpart Korean Patent Application No. KR10-2012-0049732 (5 pages, in Korean).
(Continued)

*Primary Examiner* — Lisa Caputo
*Assistant Examiner* — Brandi Hopkins
(74) *Attorney, Agent, or Firm* — NSIP Law

(57) ABSTRACT

Provided herein is a test equipment for evaluating safety of a piping for use in nuclear power plants, the test equipment having a test specimen made of a same material as the piping, and having a notch cut from a first surface which is an end portion of the test specimen, with a crack formed at an end portion of the notch; and a load applier connected to the test specimen to apply a load in a direction perpendicular to a direction in which the notch is cut, wherein a pair of pin holes are connected to the load applier such that they are arranged to be distanced from each other along the direction of the load applied to the test specimen, and a central point is provided in a space between a second surface opposing the first surface and an end portion of the crack.
Therefore, according to the present disclosure, there is provided a test equipment for evaluating safety of a piping capable of conducting a highly reliable safety evaluation using a test specimen having a same stress gradient as the piping actually constructed when a load is applied.

9 Claims, 6 Drawing Sheets

(56) References Cited

OTHER PUBLICATIONS

Development of Nuclear technology "Real-Scale Pipe Testing and Knowledge and Information Database on the Piping of Nuclear Power Plant for the LBB Design" (Aug. 27, 2009) In Korean, including partial English Translation; (Total 225 pages, see p. 30-31).

* cited by examiner

Fig 3.
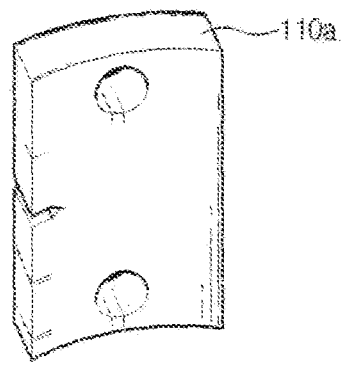
(a)
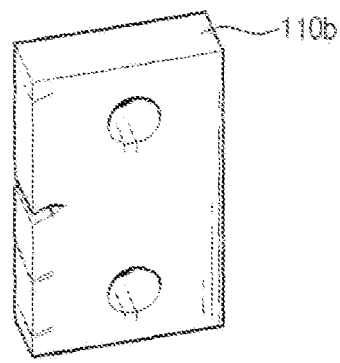
(b)
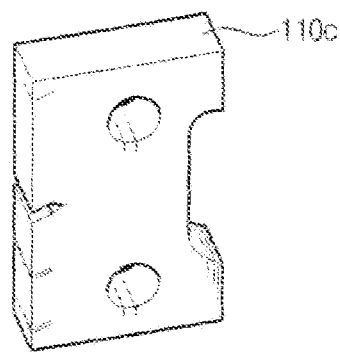
(c)

Fig 5.
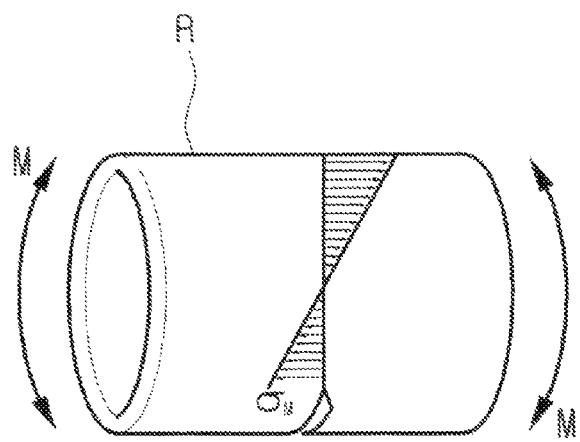
(a)
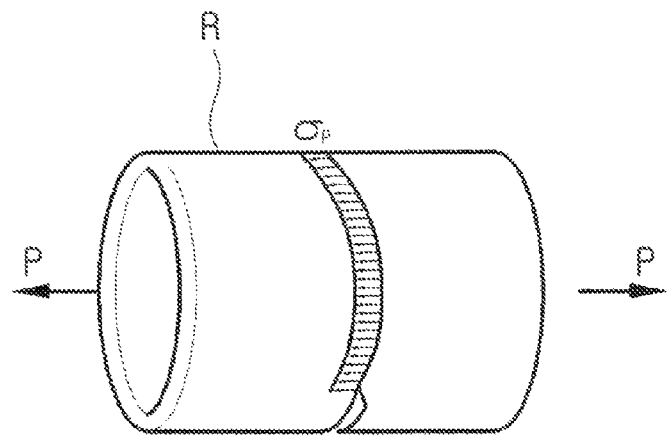
(b)
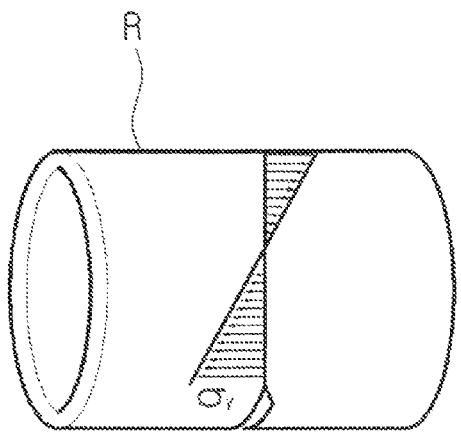
(c)

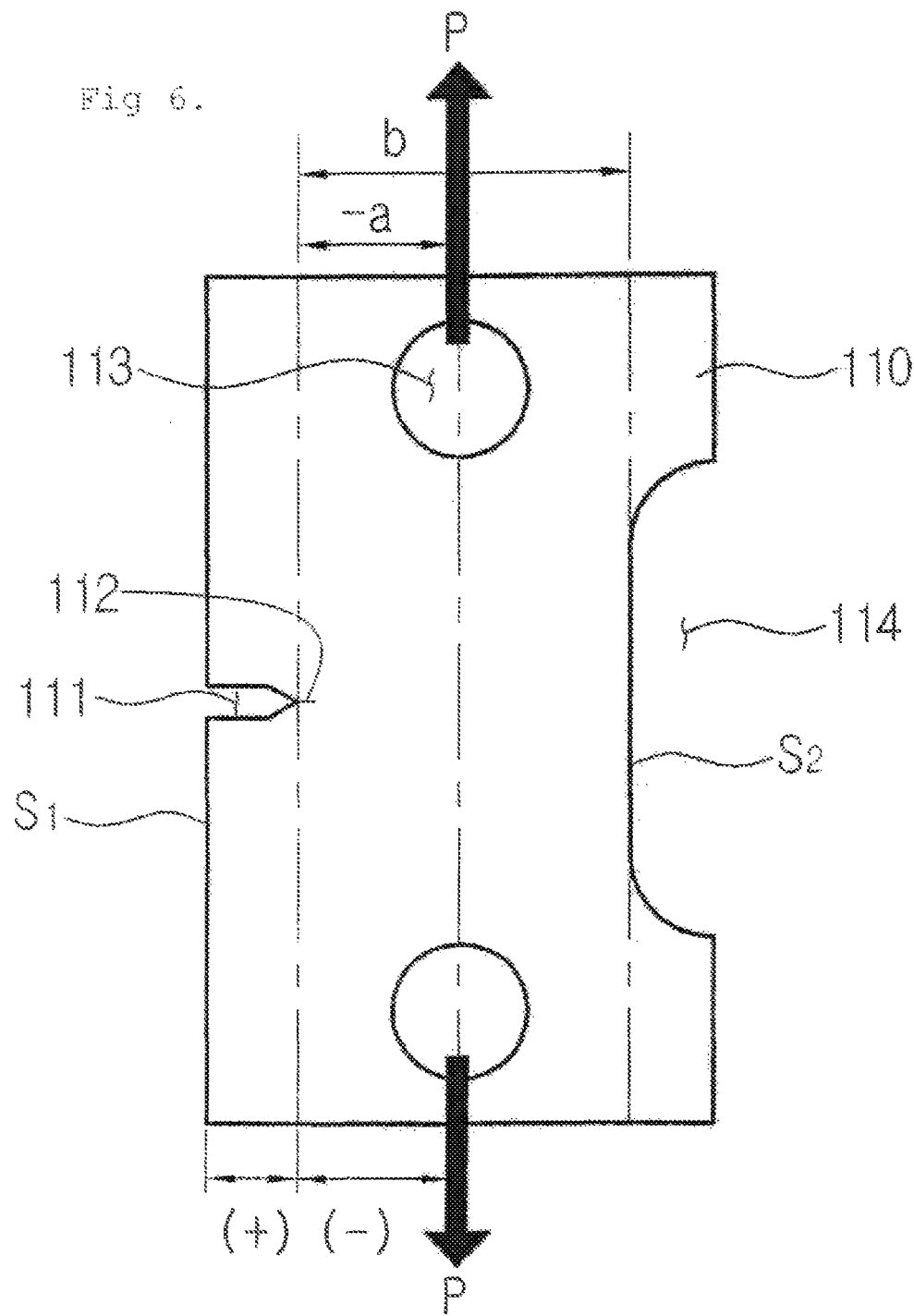

METHOD FOR MAKING TEST SPECIMEN AND TEST EQUIPMENT TO EVALUATE THE SAFETY OF PIPING

CROSS-REFERENCE TO RELATED APPLICATIONS

This application claims the benefit of priority under 35 U.S.C. §119(a) of Korean Patent Application No. 10-2012-0049732, filed on May 10, 2012, in the Korean Intellectual Property Office, the entire disclosure of which is incorporated herein by reference for all purposes.

BACKGROUND

1. Field

The following description relates to a method for making a test equipment and a test specimen for evaluating the safety of a piping, for example, to a method for making a test equipment capable of evaluating the safety of a piping and a test specimen to be used in the test equipment.

2. Description of Related Art

When designing a nuclear power plant, in order to prevent 2nd and 3rd serial break after a double ended guiliotine break (DEGB) of a high energy pipeline, massive protective walls, pipe restraints, and fluid jet preventing walls are built, and the costs for such safety designing accounts for 30% of the total designing costs.

However, when a leakage occurs before a double ended guiliotine breack (DEGB) occurs, and thus stops operation of the nuclear power plant, it is possible to save additional costs. This is called the "Leakage Before Break (LBB) Designing". Especially, applying the "Leakage Before Break (LBB) Designing" concept when constructing a nuclear power plant is known to have hundreds of billions of economic profits per unit of power plant.

However, what is essential in applying the "Leakage Before Break (LBB) Designing" concept is the J-R Curve regarding the subject piping, which until now was calculated using a compact tension specimen (CT specimen) of a thickness of 1 inch (25.4 cm).

FIG. 1 illustrates an example of a conventional test specimen for evaluating safety of a piping.

However, conventional test specimens 10a, 10b, 10c illustrated in FIG. 1 show different J-R Curves depending on their sizes, and these J-R Curves are known to be different from the J-R Curves of real scale piping, and thus there is a problem that safety evaluation using conventional test specimen lacks reliability.

Furthermore, in some cases, an actual piping is used in conducting a J-R Curve test in order to obtain reliability in safety evaluation tests, but this costs too much and the test is more difficult.

SUMMARY

Therefore, the purpose of the present disclosure is to resolve the aforementioned problem, that is, to provide a test equipment for evaluating safety of a piping capable of conducting a highly reliable safety evaluation using a test specimen having the same stress gradient as the piping actually constructed when a load is applied, and a method for making the test specimen.

In one general aspect, there is provided a test equipment for evaluating safety of piping for use in nuclear power plants, the equipment comprising: a test specimen made of a same material as the piping, and having a notch cut from a first surface which is an end portion of the test specimen, with a crack formed at an end portion of the notch; and a load applier connected to the test specimen to apply a load in a direction perpendicular to a direction in which the notch is cut, wherein a pair of pin holes are connected to the load applier such that they are arranged to be distanced from each other along the direction of the load applied to the test specimen, and a central point is provided in a space between a second surface opposing the first surface and an end portion of the crack.

In addition, the test specimen may have a same thickness as the piping so that a J-R curve measured from the test specimen is identical to the actual piping.

Furthermore, the end portion of the test specimen may be processed to have a same curvature as the piping so that a J-R curve measured from the test specimen is identical to the actual piping.

In addition, second surface of the test specimen may form a dent dented towards inside so as to prevent the pin holes from breaking when a load is applied from the load applier.

In another general aspect, there is provided a method for producing a test specimen for use in a test equipment for evaluating safety of piping according to any one of claims 1 to 4, the method comprising: preparing a test specimen made of a same material as a piping actually constructed; forming a notch by cutting a portion of the test specimen from one end portion towards inside; forming a crack at an end portion of the notch; and forming a pair of pin holes in an area between another end portion of the test specimen and the crack to be distanced from each other, wherein the notch, the crack, and the pin holes are processed so that a stress gradient measured from the test specimen is identical to a stress gradient of the actual piping.

In addition, the preparing a test specimen may be characterized to process the end portion of the test specimen to have a same curvature as the actual piping According to the present disclosure, there is provided a test equipment for evaluating safety of a piping capable of evaluating safety where a test specimen copies an actual test specimen most closely by having pin holes between the notch and the end portion of the test specimen so that the test specimen has the same stress gradient as when a load is applied.

Furthermore, by copying the actual piping instead of using the actual piping, it is possible to save evaluation costs.

In addition, according to the present disclosure, there is provided a method for easily making a test specimen for evaluation safety of a piping, the test specimen have a same stress gradient as the actual piping.

In addition, the present disclosure enables obtaining a test specimen having a same J-R Curve as the actual piping, thereby improving reliability of the safety test through the test specimen.

BRIEF DESCRIPTION OF THE DRAWINGS

FIG. 3 illustrates various exemplary embodiments of a test specimen of a test equipment for evaluating safety of a piping of FIG. 2;

FIG. 5 is for explaining a stress gradient applied to an actually constructed piping; and FIG. 6 is a front view of a test specimen for explaining a method for making a test specimen for evaluating safety of a piping of FIG. 4.

Figure 1:
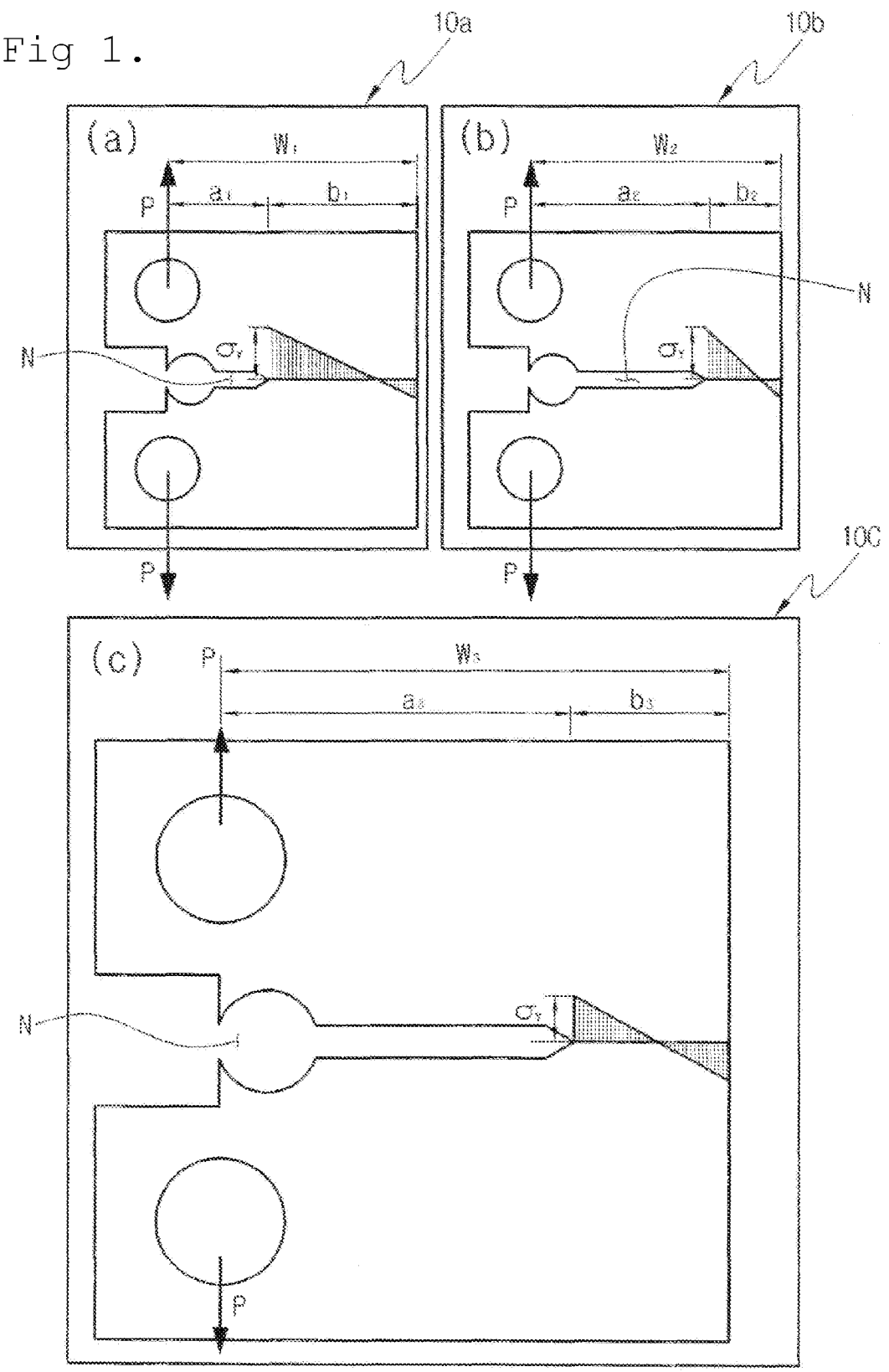
FIG. 1 illustrates an example of a conventional test specimen for evaluating safety of a piping.

Throughout the drawings and the detailed description, unless otherwise described, the same drawing reference numerals will be understood to refer to the same elements, features, and structures. The relative size and depiction of these elements may be exaggerated for clarity, illustrating, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Figure 2:
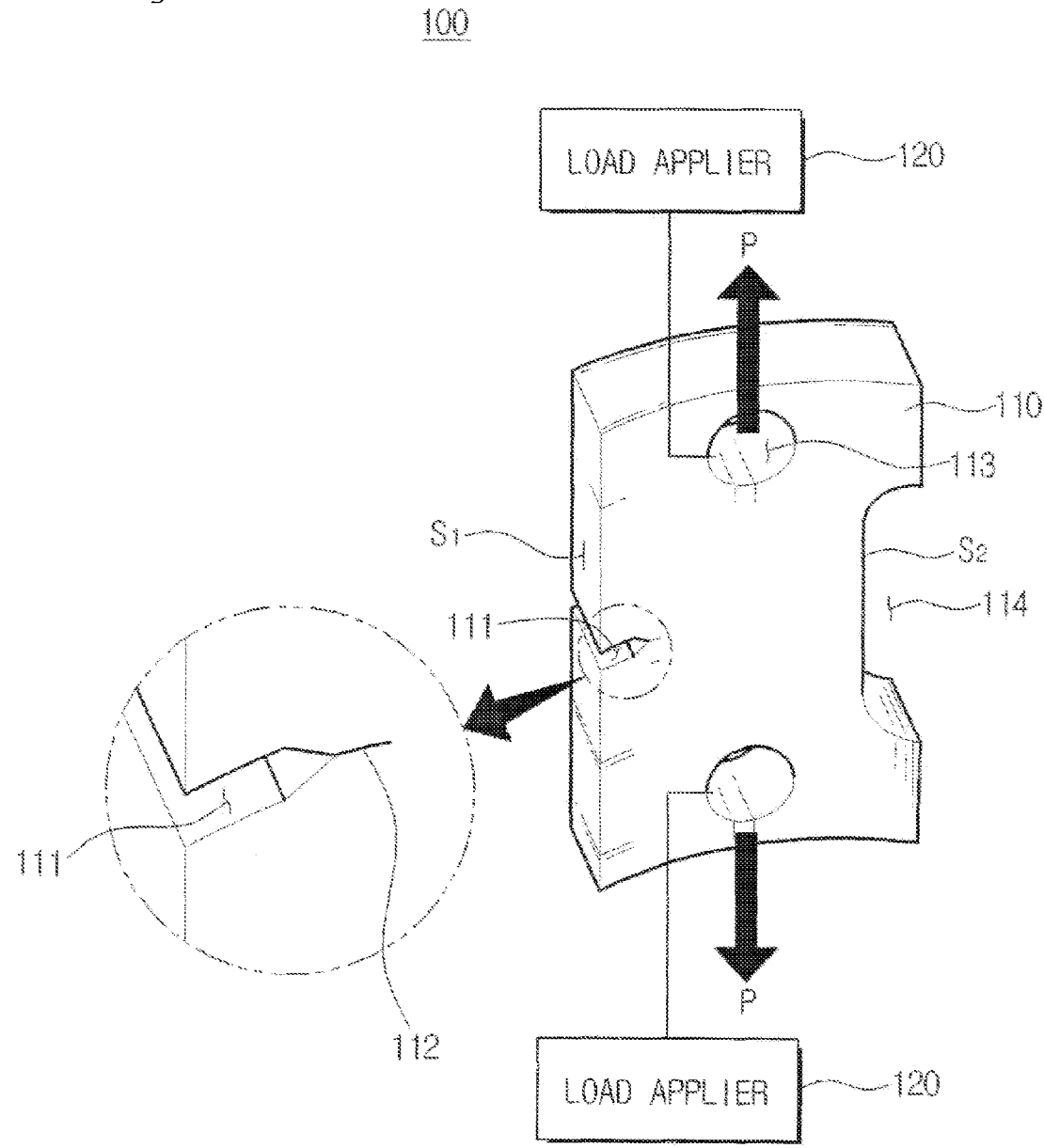
FIG. 2 roughly illustrates a test equipment for evaluating a piping according to an exemplary embodiment of the present disclosure.

FIG. 2 roughly illustrates a test equipment for evaluating safety of a piping according to an exemplary embodiment of the present disclosure.

With reference to FIG. 2, a test equipment 100 for evaluating safety of a piping according to an exemplary embodiment of the present disclosure relates to a test equipment copying a same stress gradient as that of an actual piping constructed in a nuclear power plant, thereby improving the test reliability. The test equipment 100 includes a test specimen 110 and a load applier 120.

The test specimen 110 receives a load P from the load applier 120 to be explained hereinbelow and copies an actual piping constructed in nuclear power plants etc. to evaluate safety of the piping P, and thus is preferably made of a same material as the actual piping.

Meanwhile, a specific shape and structure of the test specimen 110 are explained hereinbelow with one surface of the test specimen 110 defined as a first surface $S_1$, and another surface facing the first surface $S_1$ as a second surface $S_2$.

On the test specimen 110, there is a notch 111 cut to have a predetermined length from the first surface $S_1$ towards the second surface $S_2$, and on one end portion of the notch 111, a crack 112 is formed.

In addition, in order to receive a load P, a pair of pin holes 113 are formed on the test specimen 110 distanced from each other and connected to the load applier 120. The pin holes 113 are distanced by a predetermined distance along a longitudinal direction of the test specimen 110, and in the present exemplary embodiment, the cross section of the pin holes 113 is a circle having a predetermined diameter, but it is preferably determined considering the shape of a predetermined pin to be inserted into and mounted on the pin holes 113 and connected to the load applier 120 to be explained hereinbelow.

Herein, a central point of the pin holes 113 is provided in a distanced space between the crack 112 and the second surface $S_2$, that is the distanced space between the surface extended from the end portion of the crack 112 along a longitudinal direction of the test specimen 110 and the second surface $S_2$ so that the test specimen 110 can have a same stress gradient as the stress gradient of an actual piping by the load P applied from the load applier 120.

In addition, the diameter of the pin holes 120 formed on the test specimen is not limited thereto, and in order to prevent the pin holes 113 from breaking by a load P in a case where the size of the pin holes 113 is increased, a portion of the second surface $S_2$ is dented towards the first surface $S_1$, forming a dent 114 on a side surface of the test specimen 110.

Meanwhile, locations of the notch 111, crack 112, and pin holes 113 of the test specimen 110 are designed to be formed at appropriate locations in order to precisely copy the stress gradient of an actual piping. A method for processing and designing such a test specimen 110 is explained hereinbelow with reference to an explanation on a method for making a test specimen for evaluating safety of a piping.

The load applier 120 is directly connected to the pin holes 113 formed on the test specimen 110. The load applier 120 is a device for applying a load P to the test specimen 110.

Meanwhile, FIG. 3 illustrates various exemplary embodiments of a test specimen of a test equipment for evaluating safety of a piping of FIG. 2, and as illustrated in FIG. 3, the test specimen used in the present disclosure may be embodied in various shapes depending on necessity such as a shape having a curvature but not a dent 110a, a flat panel shape not having a dent 110b, and a flat panel shape having a dent 110c.

Hereinbelow is explanation on an exemplary embodiment of a method for making the aforementioned test specimen for evaluating safety of a piping.

Figure 4:
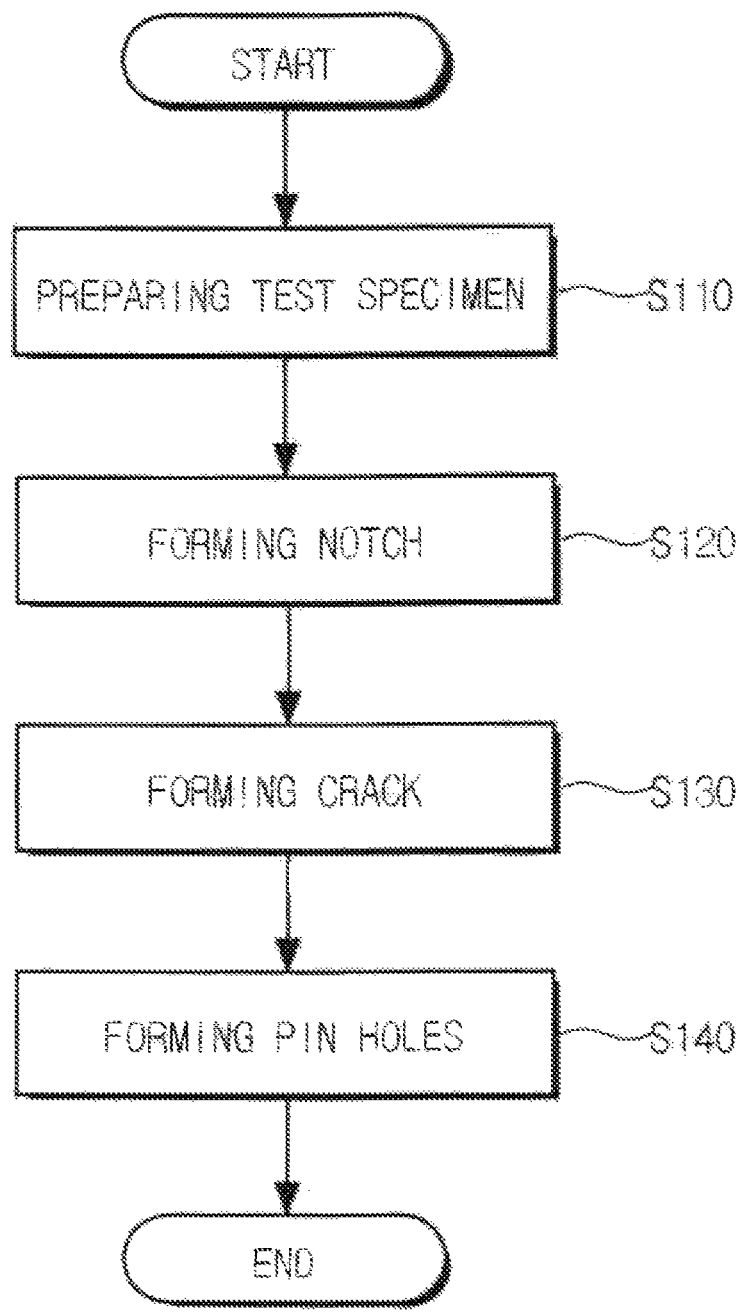
FIG. 4 roughly illustrates a process flowchart of a method for making a test specimen for evaluating safety of a piping according to an exemplary embodiment of the present disclosure.

FIG. 4 roughly illustrates a process flowchart of a method for making a test specimen for evaluating safety of a piping according to an exemplary embodiment of the present disclosure; FIG. 5 is for explaining a stress gradient applied to an actually constructed piping; and FIG. 6 is a front view of a test specimen for explaining a method for making a test specimen for evaluating safety of a piping of FIG. 4.

With reference to FIG. 4, a method for making a test specimen for evaluating safety of a piping according to an exemplary embodiment of the present disclosure (S100) is a method for making a test specimen designed in such a manner to copy a same stress gradient as one applied to an actually constructed piping in a nuclear power plant, and the method includes preparing a test specimen (S110), forming a notch (S120), forming a crack (S130), and forming pin holes (S140).

The preparing a test specimen (S110) is a step for preparing a test specimen 100. The test specimen 110 in this step is made of a same material as the aforementioned actual piping, and especially, is preferably made to have a same thickness as the actual piping in order to improve the test reliability through precise copying of the piping.

In addition, in this step, the test specimen 110 is processed to have a same curvature as the curvature formed in the actual piping. That is, the test specimen 110 should be processed so that the test specimen 110 finally made could have a same curvature as the actual piping.

The forming a notch (S120) is a step of forming a notch 111 on the test specimen 110 processed and prepared at the aforementioned step of preparing a test specimen (S110).

Defining one cross section of the test specimen 110 as a first surface S1 and another cross section opposing the same as a second surface S2, in this step, a notch 111 is processed by cutting a portion of the first surface $S_1$ of the test specimen 110 towards the second surface $S_2$. That is, the notch 111 is extended along a perpendicular direction to a load P being applied to the test specimen 110.

Herein, the width and length of the cut of the notch 111 processed in this step are preferably determined comprehensively considering the size of the applied load P, size of the test specimen 110, and stress gradient measured from the actual piping.

The forming a crack (S130) is a step of forming a crack 112 to extend from a final end portion of the notch 111 towards the second surface $S_2$. That is, this is a step of processing a crack 112 to have a smaller width than the notch 11, the crack 112 being a location where a load corresponding to a yield stress is applied and thus a crack is initiated.

The forming pin holes (S140) is a step of processing pin holes 113 which is a space where a pin to be connected with the load applier 120 would be mounted and installed, so as to apply a pin load to the test specimen 110. It is a step of processing a pair of pin holes 112 having the shape of a predetermined diameter on the test specimen 110.

Meanwhile, locations of the notch 111, crack 112, and pin holes 113 processed at the aforementioned step of forming a notch (S120), step of forming a crack (S130), and step of forming pin holes (S140), respectively are determined considering a stress gradient of an actual piping. And the method for determining these locations will be explained hereinbelow.

FIG. 5 is for explaining a stress gradient applied to an actually constructed piping.

With reference to FIG. 6, hereinbelow is explanation on a test specimen 110 made in the method of the present exemplary embodiment on the assumption that, as illustrated in FIG. 5, a bending moment M and a tensile strength P are applied to an actual piping R at the same time, and the same bending moment M and the tensile strength P are applied to the test specimen.

First of all, a section modulus Z of a test specimen made in the present exemplary embodiment may be represented as in the following [Mathematical equation 1].

$$Z = \frac{Bb^2}{6} \quad \text{[Mathematical equation 1]}$$

Herein, B is a thickness of the test specimen 10 of the present exemplary embodiment, b is a distance between a final end portion of the notch 111 and a second surface $S_2$.

Therefore, the bending moment M by the load P applied to the test specimen 110 may be represented as in the following [Mathematical equation 2].

$$M = P\left(a + \frac{b}{2}\right) = P\left(\frac{2a+b}{2}\right) \quad \text{[Mathematical equation 2]}$$

Herein, a represents a coordinate value of the central point of the pin holes 113, and a is defined to have a negative (−) value in the second surface $S_2$, and a positive (+) value in the first surface $S_1$ direction, with the final end portion of the notch 111 in a coordinate system set with the final end portion of the notch 111 as the reference point. That is, when the central point of the pin holes 113 is located on the second surface $S_2$ from the final end portion of the notch 111, a has a negative (−) value.

Therefore, a maximum stress $\sigma_M$ by the applied bending moment may be represented as in the following [Mathematical equation 3].

$$\sigma_M = \frac{M}{Z} = \frac{P\frac{2a+b}{2}}{Bb^2} = \frac{3P(2a+b)}{Bb^2} \quad \text{[Mathematical equation 3]}$$

In addition, the tensile stress $\sigma_P$ the load P may be represented as in the following [Mathematical equation 4].

$$\sigma_P = \frac{P}{A} = \frac{P}{bB} \quad \text{[Mathematical equation 4]}$$

Therefore, the maximum stress $\sigma_{max}$ and the minimum stress $\sigma_{min}$ applied by the applied load may be represented as in the following [Mathematical equation 5] and [Mathematical equation 6].

$$\sigma_{max} = \sigma_M + \sigma_P = \frac{2P[3a+2b]}{Bb^2} \quad \text{[Mathematical equation 5]}$$

$$\sigma_{min} = -\sigma_M + \sigma_P = \frac{-2P[3a+b]}{Bb^2} \quad \text{[Mathematical equation 6]}$$

Herein, assuming that the maximum stress $\sigma_{max}$ is the same as the yield strength $\sigma_Y$ of the test specimen, the minimum stress $\sigma_{min}$ and the yield strength $\sigma_Y$ may be represented as in the following [Mathematical equation 7].

$$\sigma_{min} = \frac{-\sigma_Y[3a+b]}{3a+2b} \quad \text{[Mathematical equation 7]}$$

Therefore, the difference between the maximum stress $\sigma_{max}$ and the minimum stress $\sigma_{min}$ applied to the test specimen 110 may be represented as in the following [Mathematical equation 8].

$$\sigma_{max} - \sigma_{min} = \sigma_Y + \frac{\sigma_Y(3a+b)}{3a+2b} = \sigma_Y \cdot \frac{6a+3b}{3a+2b} \quad \text{[Mathematical equation 8]}$$

Therefore, the stress gradient $S_s$ applied to the test specimen 110 may be represented as in the following [Mathematical equation 9] by the aforementioned [Mathematical equation 8].

$$S_S = \frac{\Delta\sigma}{b} = \frac{3(2a+b)}{b(3a+2b)}\sigma_Y = \frac{3\sigma_Y(2a+b)}{b(3a+2b)} \quad \text{[Mathematical equation 9]}$$

Therefore, using the aforementioned [Mathematical equation 9], it is possible to adjust and process a location b of the notch and a location a of the pin holes so that the test specimen 110 could have a same stress gradient as that applied to an actual piping.

Stress gradients actually measured in the piping being actually constructed and used are usually close to 0, and thus when this is applied to a test specimen finally made in the present exemplary embodiment, since b represents the distance between the end portion of the notch 111 and the second surface $S_2$, it is a positive (+) value, and thus in order to have a offset b so that the stress gradient $S_s$ of the test specimen is closed to 0, a becomes to have a negative (−) value.

Therefore, as aforementioned, in order to copy the stress gradient of an actual piping, the location a of the coordinate of the central point of the pin holes 113 has a negative value, and according to the coordinate set as aforementioned, the central point of the pin holes 113 is located in the space between the notch 111 and the second surface $S_s$.

That is, by adjusting and processing the location of the pin holes 113 and the notch 111 in [Mathematical equation 9], it is possible to make a test specimen precisely copying the stress gradient of an actual piping.

In other words, the test specimen made according to the present exemplary embodiment may precisely copy the stress gradient of an actual piping, and accordingly, it is possible to obtain a same J-R Curve as an actual piping from the test specimen made according to the present exemplary embodiment.

Therefore, it is possible to improve the reliability of safety evaluated from such a specimen.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

DESCRIPTION OF REFERENCE NUMERALS

110: Test Specimen
120: Load Applier
111: Notch
112: Crack
113: Pin Holes

What is claimed is:

1. A test equipment for evaluating piping safety for use in nuclear power plants, the test equipment comprising:
   a test specimen comprising a same material as the piping, and having a notch cut from a first surface, with a crack formed at an end portion of the notch; and
   a load applier connected to the test specimen to apply a load in a direction perpendicular to a direction in which the notch is cut,
   wherein a pair of pins are connected to the load applier though pin holes disposed within the test specimen and perpendicular to the direction in which the notch is cut such that the pin holes are arranged to be distanced from each other along the direction of the load applied to the test specimen, and the pin holes are arranged in a space between a second surface of the test specimen and an end portion of the crack, whereby a stress gradient measured from the test specimen is identical to a stress gradient of the piping.

2. The test equipment according to claim 1, wherein the test specimen has a same thickness as the piping so that a J-R curve measured from the test specimen is identical to the piping.

3. The test equipment according to claim 2, wherein an end portion of the test specimen is processed to have a same curvature as the piping so that a J-R curve measured from the test specimen is identical to the piping.

4. The test equipment according to claim 3, wherein the second surface of the test specimen forms a dent dented towards an inside of the test specimen to prevent the pin holes from breaking when a load is applied from the load applier.

5. The test equipment according to claim 1, wherein a cross-section of the pin holes is based on a shape of respective pins to be inserted therein, and mounted within the pin holes and connected to the load applier.

6. The test equipment according to claim 1, wherein a width and length of the cut of the notch is based on a size of the applied load P, a size of the test specimen, and a stress gradient measured from the piping.

7. A method for producing a test specimen configured to be used in a test equipment for evaluating of piping safety, the method comprising:
   preparing a test specimen comprising a same material as a pipe;
   forming a notch by cutting a portion of the test specimen from one end portion of the test specimen towards an inside of the test specimen;
   forming a crack at an end portion of the notch; and
   forming a pair of pin holes in an area between another end portion of the test specimen and the crack so that the pin holes are disposed within the test specimen and perpendicular to a direction in which the notch is cut and distanced from each other along a direction of a load applied to the test specimen, whereby a stress gradient measured from the test specimen is identical to a stress gradient of the pipe.

8. The method according to claim 7, wherein an end portion of the test specimen has a same curvature as the pipe.

9. The method according to claim 7, further comprising adjusting and processing a location of the notch and a location of the pin holes so that the test specimen has the same stress gradient as that applied to the pipe based on $$S_S = \frac{\Delta\sigma}{b} = \frac{3(2a+b)}{b(3a+2b)}\sigma_Y = \frac{3\sigma_Y(2a+b)}{b(3a+2b)}$$

where $S_s$ is the stress gradient of the test specimen, $\Delta\sigma$ is the change in stress, $\sigma_Y$ is the yield strength of the test specimen, 'a' is a location of the pin holes, and 'b' is a location of the notch.

* * * * *